United States Patent [19]

Li et al.

[11] 4,137,421

[45] Jan. 30, 1979

[54] PURIFICATION OF DICHLOROETHYLENE COMPOUND

[75] Inventors: Ming K. Li, Schenectady; Michael R. MacLaury, Rexford, both of N.Y.

[73] Assignee: General Electric Company, Schenectady, N.Y.

[21] Appl. No.: 879,083

[22] Filed: Feb. 21, 1978

[51] Int. Cl.² ............................................. C07C 37/24
[52] U.S. Cl. ................................................... 568/725
[58] Field of Search ................................ 568/725, 726

[56] References Cited

U.S. PATENT DOCUMENTS

| 2,329,074 | 9/1943 | Muller | 568/726 |
| 4,073,814 | 2/1978 | Kinson et al. | 568/726 |

Primary Examiner—Norman Morgenstern
Attorney, Agent, or Firm—Joseph T. Cohen; Charles T. Watts

[57] ABSTRACT

Impure 1,1-dichloro-2,2-bis(4-hydroxyphenyl)ethylene can be purified by heating the latter either with phenol alone or with a mixture of methylene chloride and phenol, allowing the heated mixture to cool until crystallization occurs and removing the above-identified purified dichloroethylene compound.

6 Claims, No Drawings

PURIFICATION OF DICHLOROETHYLENE COMPOUND

This invention is concerned with a process for purifying a specific dichloroethylene compound. More particularly, the invention relates to a process for purifying crude 1,1-dichloro-2,2-bis(4-hydroxyphenyl)ethylene (hereinafter designated as "BPC" or the impure product as "crude BPC") having the formula

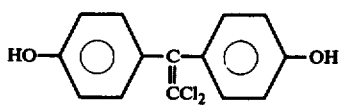

I which has been prepared by a sequence involving first the reaction of phenol and chloral in the presence of an acidic condensing agent, such as sulfuric acid, to form the precursor trichloro-ethane compound, 1,1,1-trichloro-2,2-bis(4-hydroxyphenyl)ethane, having the formula

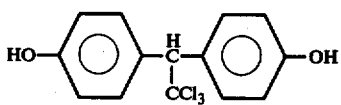

II and then the latter is dehydrohalogenated to form the crude BPC of formula I by the use of, for instance, an alkali-metal hydroxide, such as KOH and methanol as more particularly described in Polish Pat. No. 70,073 published Sept. 8, 1975. In accordance with the claimed invention, the crude BPC is heated at elevated temperatures with phenol until solubilization of the BPC is effected and thereafter cooling the homogeneous mixture to effect precipitation of the BPC in the form of a crystalline product which, upon isolation, will yield a BPC of considerably higher purity than the starting crude BPC. The invention also embraces an improvement whereby methylene chloride is used in combination with the phenol, and by the use of elevated temperatures and pressures, BPC of still higher purity and often somewhat better yields can be realized. The use of methylene chloride with the phenol permits more facile processing of the mixture of ingredients during the filtration and isolation steps then when the methylene chloride is omitted.

The dichloroethylene compound of formula I is used in making polycarbonate resins by reacting this compound with phosgene to form polymeric compositions composed of recurring structural units of the formula

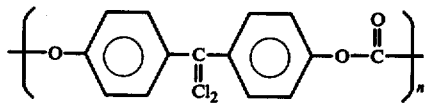

where $n$ is a whole number greater than 1. Such polymers have been found to have exceptionally good flame retardancy. For this reason, these polycarbonate resins have wide application where flame retardancy, and particularly a high oxygen index, is desired.

In preparing the monomeric dichloroethylene compound of formula I, the impure or crude monomer contains a number of impurities in amounts ranging up to 2–3%, by weight, of the BPC, which, if allowed to remain in the BPC, could adversely affect the physical properties of the polycarbonate composition made therefrom. Among the impurities which have been found to be in significant amounts in the crude BPC, are those having the formula [1-chloro-2,2-bis(4-hydroxyphenyl)ethylene]

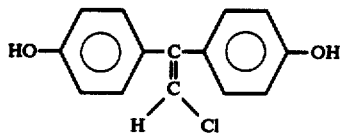

III and traces of the trichloro-ethane of formula II.

Unexpectedly, we have discovered that the BPC has adequate solubility in phenol at elevated temperatures and, when such solutions are cooled, much of the impurities remains dissolved in the phenol, and the BPC settles out as a substantially white crystalline product. The mother liquor phenol obtained after removing the BPC crystals, for instance, by filtration, may be recycled and reused either in making additional trichloroethane of formula II by reaction with chloral, or can be reused with additional crude impure BPC for crystallization of the latter to the purified state. This is possible because, unexpectedly, the BPC and the phenol do not form an adduct similar to that which is obtained when bisphenol-A having the formula

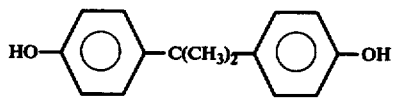

is purified with phenol by treating the bisphenol-A with the phenol and then causing the phenol adduct (which has a ratio of about 1 phenol molecule per bisphenol-A molecule) to be reduced to the bisphenol-A itself by treatment with water as described, for instance, in U.S. Pat. No. 2,791,616 — Luten. In this respect, the use of phenol for purifying the BPC proceeds by an entirely different route than does the purification of bisphenol-A with phenol described in the aforesaid Luten patent.

In carrying out the purification step of the BPC, the crude BPC and phenol are heated under an inert atmosphere, such as nitrogen, to a temperature at which the BPC is dissolved in the phenol. This may require temperatures of the order of at least 50° C. up to decomposition point of the BPC. Advantageously temperatures below 200° C. should be used, e.g., from 50° to 190° C. depending on the amount of phenol used. The more phenol that is used with the crude BPC, substantially lower temperatures are possible for effecting solubilization of the BPC in the phenol. Thus, on a weight basis, one can employ from about 1 to 5 parts or more of the phenol per part of the crude BPC. If lower proportions of phenol are used with respect to the amount of crude BPC, although higher temperatures of solubilization may be required, it has also been found that the yield of the purified BPC is improved. After cooling the mixture of the crude BPC and phenol to around 30° to 50° C., the mixture is usually in the form of a slurry which can be filtered for instance, in a Buchner funnel, and thereafter washed with a suitable solvent, for instance, methylene chloride. The crystals remaining after removal of the phenol, after drying, are white in appearance. Further heating of the crystalline product and then air drying (or by the use of vacuum) will usually remove further traces of phenol and any wash material which may have been left behind, thus providing a highly purified BPC.

We have also unexpectedly discovered that still further improvements in the purity of the crude BPC and some improvements in processing and yield of the purified BPC can be obtained by taking advantage of the solubility of the crude BPC in the phenol and using methylene chloride with the phenol; this permits such a combination to remove more of the impurities than when the methylene chloride is omitted. By combining the crude BPC with the mixture of the phenol and methylene chloride, and heating the combination of ingredients at elevated temperatures and also at elevated pressures to effect solubilization of the BPC, and thereafter cooling the mixture, a more effective removal of the impurities can be obtained while at the same time causing the formation of larger crystals of the BPC (which aids in the filtration of the purified BPC and subsequent handling). The crystals thus obtained are substantially white in appearance and the yield of the purified BPC can be as high as 90% or even more. The use of the methylene chloride also permits employing smaller amounts of phenol in the purification process, thus reducing to a considerable extent amounts of BPC which may be dissolved and lost in the phenol mother liquor. By using larger amounts of the methylene chloride, in combination with elevated temperatures and pressures, it is therefore possible to use smaller weight ratios of phenol to the crude BPC.

If the phenol should be omitted and it should be desired to effect solubilization of the crude BPC in methylene chloride alone, it was found necessary to go to a temperature of around 190° C. and 130 psi pressure. This is not too practical in commercial operation, and by using the phenol in combination with the methylene chloride, much lower temperatures and pressures can be employed to obtain the purified BPC than when the phenol is omitted.

When employing the combination of the phenol and the methylene chloride in the purification process, the temperature at which the purification process is carried out should be sufficient under the prescribed pressure conditions to effect essentially complete solubilization of the crude BPC in the mixture of the phenol and methylene chloride. For this purpose, one can employ temperatures ranging from about 50° C. to below the decomposition point of any of the members of the mixed solvent system or the BPC itself. Temperatures as high as 150° to 185° C. can advantageously be employed.

The pressure at which the solubilization step is carried out when using both the phenol and the methylene chloride can be varied fairly widely, but generally, advantageously follows the elevated temperature required to effect complete solubilization of the crude BPC in the mixture of the methylene chloride and the phenol. For this purpose, depending on the temperature used, one can employ pressures ranging from about 10 to 200 psi, and advantageously within the range from about 20 to 100 psi.

Whether or not the methylene chloride is used with the crude BPC in effecting purification of the latter, the amount of phenol used should range, on a weight basis, from about 1 to 5 parts or more of the latter per part of the crude BPC. When using the combination of the methylene chloride and the phenol for purification purposes, one can use from 1 to 10 or more parts of the methylene chloride per part of phenol; the use of larger proportions of methylene chloride to phenol yields larger and better formed crystals of the purified BPC. On a weight ratio, when using both the methylene chloride and the phenol, one can employ from 5 to 20 or more parts of the mixture of the phenol and methylene chloride per part of the crude BPC. After the purification reaction has been carried out and the mixture of ingredients has been cooled to room temperature, the white crystalline product which settles out can be removed by filtration and again washed with methylene chloride to provide whatever purification is possible by this extra wash, and the crystals dried preferably in vacuum at 60° C. to yield BPC substantially free of impurities normally associated with the starting BPC.

In order that those skilled in the art may better understand how the present invention may be practiced, the following examples are given by way of illustration and not by way of limitation, of using the phenol alone for purification purposes and also of using both the phenol and methylene chloride for purification purposes.

The presence of the impurities of formulas II and III was determined by analyzing with a high pressure liquid chromatograph; the colored impurities were determined by observing the "Absorbance" of 1.5 grams of BPC in 10 ml methanol measured at 425 nm in a 1 cm path length cell; the lower the absorbance value the less color in the product. The heating to effect solubilization was carried out under a nitrogen atmosphere only in those cases where methylene chloride was used. The crude BPC used in the following examples was obtained by reacting phenol and chloral in approximately a 2:1 molar ratio in the presence of sulfuric acid and then dehydrohalogenated with ammonia as described in the pending U.S. patent application Ser. No. 771,208 filed Feb. 23, 1977, and assigned to the same assignee as the present invention. By reference, this application is made part of the disclosures of the instant application. This will yield crude BPC containing up to 2-3% of the two impurities of formulas II and III.

EXAMPLE 1

Crude BPC and phenol in varying weight ratios were placed in a reaction vessel equipped with a condenser and a stirrer. The mixtures were heated to a temperature at which the crude BPC dissolved in the phenol. Thereafter, each crude BPC/phenol mixture was cooled to about 45° C. The slurry which was obtained was filtered on a Buchner funnel and the crystals which remained on the funnel were washed with methylene chloride. The material was then dried in air to produce an essentially white crystalline material. The following Table I shows the results of varying the weight ratio of phenol to crude BPC, and varying the heating temperature.

TABLE I

| Test No. | Phenol/ Crude BPC Wt. Basis | cHeating Temp. °C | Absorbance | aImpurities Parts/Million | | bPercent Recovery |
|---|---|---|---|---|---|---|
| | | | | Compound Formula II | Compound Formula III | |
| 1 | Crude BPC | — | 0.66 | 15000 | 560 | — |
| 2 | 90.02:9.98 | 75 | 0.007 | 320 | 100 | 34.2 |
| 3 | 79.45:20.45 | 108 | 0.011 | 1080 | 80 | 63.8 |

TABLE I-continued

| Test No. | Phenol/ Crude BPC Wt. Basis | [c]Heat-ing Temp. °C | Ab-sorb-ance | [a]Impurities Parts/Million Compound Formula II | Compound Formula III | [b]Per-cent Re-covery |
|---|---|---|---|---|---|---|
| 4 | 69.92:30.08 | 127 | 0.013 | 1580 | 100 | 76.4 |

[a]The impurity values (parts/million) were determined on the basis of 10μ 1 injection of 0.1 g/1.0 ml crude BPC-methanol solution.
[b]Based on final solid weight to the original crude BPC weight, the final solid being crystallized (i.e., cooled) at 45° C.
[c]Temperature at which mixture dissolved.

The following examples illustrate the use of methylene chloride in combination with phenol for purification of the crude BPC.

EXAMPLE 2

About 5 grams (0.0178 mol) BPC and 13.6 grams (0.145 mol) phenol were suspended in 20 ml methylene chloride all placed in a pressure vessel. The pressure vessel was closed and heated under nitrogen to a temperature of about 110° C. at about 40 psi, at which point the mixture formed a homogeneous solution. Upon cooling this solution to room temperature, a white crystalline product was obtained which when removed and washed with methylene chloride and dried in vacuum at 60° C. yielded 4.0 grams (80% yield) of essentially pure BPC, substantially free of impurities normally associated with the starting BPC.

The methylene chloride-phenol mother liquor mixture was removed and the methylene chloride was distilled under reduced pressure. The residue was found to be a mixture of phenol and BPC and weighed about 14.6 grams (containing about 1 gram BPC). This phenol/BPC residue was recycled twice more with 5 gram portions of impure BPC and 25 ml and 50 ml methylene chloride, respectively. The following Table II shows the yield and purity as a result of this series of purifications.

TABLE II

| Test No. | Yield of Purified BPC | Ab-sorbance | Impurities Parts Per Million Compound Formula III | Compound Formula II |
|---|---|---|---|---|
| 5 | [c]Starting BPC | 0.275 | 250 | 650 |
| 6 | 80% BPC | 0.018 | 50 | 300 |
| 7 | [a]98% BPC | 0.030 | 80 | 300 |
| 8 | [b]100% BPC | 0.046 | 120 | 300 |

[a]Used 25 ml CH$_2$Cl$_2$.
[b]Used 50 ml CH$_2$Cl$_2$.
[c]Different crude BPC from Example 1.

EXAMPLE 3

In this example, phenol and crude BPC (same as used in Example 2) were suspended with 50 ml methylene chloride in the same manner as Example 2, but this time using 6 mols of the phenol per mol of the crude BPC. The mixture was heated to 145° C. at 55 psi until full solubility of the BPC in the solvent mixture was attained. Thereafter, the mixture of ingredients was cooled to room temperature, at which point crystals of BPC precipitated. The filtrate consisting of the phenol and methylene chloride together with residual BPC was recycled two more times with 5 gram portion of starting BPC and 50 ml methylene chloride. Table III recites the yield and purity of this series of purification steps.

TABLE III

| Test No. | Yield of Purified BPC | Absorbance | Parts Per Million Compound Formula III | Compound Formula II |
|---|---|---|---|---|
| 9 | 86% | 0.048 | — | — |
| 10 | 91% | 0.047 | 80 | 300 |
| 11 | [a]106% | 0.047 | — | — |
| 12 | 100% | 0.051 | 120 | 300 |

[a]Amount over 100% due to supersaturation of the crude BPC mother liquor.

The use of a greater amount of methylene chloride with the phenol resulted in larger and better formed crystals of BPC. However, it required a somewhat higher temperature in order to effect solubilization of the BPC in the mixture of the methylene chloride and phenol.

EXAMPLE 4

In this example, crude BPC (same as in Example 2) was dissolved in methylene chloride without the use of phenol; in order to accomplish this, it was necessary to heat the mixture to 190° C. at 130 psi. Although a yield of 99% purified BPC was obtained when the mixture was cooled to room temperature (and the amount of impurities was reduced), it was found that the absorbance was 0.164, higher than in any instance where the phenol was combined with the methylene chloride.

It will of course be understood by those skilled in the art that in addition to the proportion of ingredients described in the aforesaid examples, other proportions may be employed in accordance with the disclosures and teachings of the present invention without departing from the scope of the invention. In addition, higher or lower temperatures and pressures may be employed depending on the degree of purity of the BPC, the amount of phenol and methylene chloride employed, etc.

Polycarbonate resins prepared from the aforesaid purified BPC can be used in applications where resistance to heat and flame retardancy is specially desirable. Among such applications are those in automotive systems, such as dashboards, grillworks, distributor caps, interior moldings, etc.

What we claim as new and desire to secure by Letters Patent of the United States is:

1. The process for purifying a dichloroethylene compound of the formula

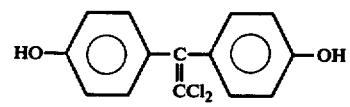

containing as impurities therein a trichloro-ethane compound of formula

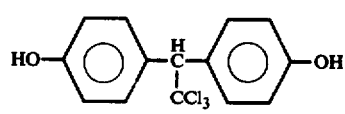

and a dichloroethylene compound of the formula

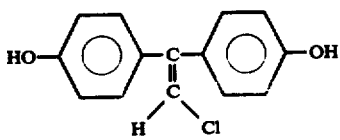

which comprises
(a) forming a mixture of the dichloroethylene compound in phenol,
(b) heating the mixture of ingredients to a temperature at which the dichloroethylene compound is substantially dissolved,
(c) cooling the mixture to a temperature at which crystals of dichloroethylene compound are produced, and
(d) removing the crystalline dichloroethylene compound of increased purity.

2. The process as in claim 1 wherein the temperature at which solution of the dichloroethylene compound in phenol is accomplished is within the range of from about 50° to 190° C.

3. The process as in claim 1 wherein the dichloroethylene compound is dissolved in a mixture of phenol and methylene chloride and the heating is conducted at superatmospheric pressure.

4. The process as in claim 3 wherein the mixture of the phenol and methylene chloride is heated to a temperature of from 50° C. to below the decomposition point of the dichloroethylene compound.

5. The process as in claim 3 wherein the mixture of ingredients is heated at a pressure of from 10 to 200 psi.

6. The process as in claim 3 wherein the mixture of the crude dichloroethylene compound, phenol and methylene chloride is heated at a temperature of from 50° to 190° C. and at a pressure of from 20 to 100 psi.

* * * * *